US008349895B2

(12) United States Patent
Van Elswyk

(10) Patent No.: US 8,349,895 B2
(45) Date of Patent: Jan. 8, 2013

(54) PRODUCTS CONTAINING HIGHLY UNSATURATED FATTY ACIDS FOR USE BY WOMEN DURING STAGES OF PRECONCEPTION, PREGNANCY AND LACTATION/POST-PARTUM

(75) Inventor: Mary Van Elswyk, Longmont, CO (US)

(73) Assignee: DSM IP Assets B.V., Heerlen (NL)

( * ) Notice: Subject to any disclaimer, the term of this patent is extended or adjusted under 35 U.S.C. 154(b) by 373 days.

(21) Appl. No.: 12/111,844

(22) Filed: Apr. 29, 2008

(65) Prior Publication Data
US 2008/0226745 A1 Sep. 18, 2008

Related U.S. Application Data

(63) Continuation of application No. 10/228,843, filed on Aug. 26, 2002, now abandoned.

(60) Provisional application No. 60/314,713, filed on Aug. 24, 2001.

(51) Int. Cl.
A61K 31/194 (2006.01)
A61K 31/202 (2006.01)
A61K 33/42 (2006.01)

(52) U.S. Cl. .......................... 514/560; 514/574; 424/602

(58) Field of Classification Search .................. 514/560, 514/574; 442/602
See application file for complete search history.

(56) References Cited

U.S. PATENT DOCUMENTS

| 4,681,896 | A | * | 7/1987 | Horrobin ...................... 514/552 |
| 4,938,984 | A | | 7/1990 | Traitler et al. |
| 5,089,268 | A | | 2/1992 | Katz |
| 5,130,242 | A | * | 7/1992 | Barclay ......................... 435/134 |
| 5,374,657 | A | | 12/1994 | Kyle |
| 5,397,591 | A | | 3/1995 | Kyle et al. |
| 5,434,183 | A | | 7/1995 | Larsson-Backstrom |
| 5,550,156 | A | | 8/1996 | Kyle |
| 5,709,888 | A | | 1/1998 | Gil |
| 5,869,530 | A | | 2/1999 | Ponroy |
| 6,022,853 | A | * | 2/2000 | Kuberasampath et al. ..... 514/12 |
| 6,117,905 | A | | 9/2000 | Higashiyama et al. |
| 6,149,964 | A | | 11/2000 | Theuer et al. |
| 6,200,624 | B1 | | 3/2001 | Mazer et al. |
| 6,258,846 | B1 | | 7/2001 | Hermelin et al. |
| 6,368,621 | B1 | | 4/2002 | Engel et al. |
| 6,576,666 | B2 | | 6/2003 | Hermelin et al. |
| 7,112,609 | B2 | | 9/2006 | Hermelin et al. |
| 2002/0044961 | A1 | | 4/2002 | Kirschner et al. |
| 2004/0101554 | A1 | | 5/2004 | Kirschner et al. |
| 2005/0037065 | A1 | | 2/2005 | Kirschner et al. |
| 2005/0101670 | A1 | | 5/2005 | Hermelin et al. |

FOREIGN PATENT DOCUMENTS

| CZ | 0281096 | 1/1996 |
| DE | 2920679 | 11/1979 |
| EP | 0404058 B1 | 11/1994 |
| EP | 0705539 A2 | 4/1996 |
| EP | 0957173 | 11/1999 |
| EP | 1194138 | 4/2002 |
| EP | 1723953 | 11/2006 |
| GB | 2044417 | 10/1980 |
| JP | 07246679 | 8/1995 |
| JP | 08230210 | 8/1996 |
| JP | 09-075000 | 3/1997 |
| JP | 10-070992 | 3/1998 |
| WO | WO 00/72831 | 12/2000 |
| WO | WO00/72842 A1 | 12/2000 |

OTHER PUBLICATIONS

Al, et al., "Long-chain polyunsaturated fatty acids, pregnancy, and pregnancy outcome", The American Journal of Clinical Nutrition, 2000, vol. 71 (suppl.), pp. 285S-291S.
Adalbjornsson, et al., "The Effects of DHA-Enriched Eggs on DHA Levels in Breast Milk", Abstracts: 91st AOCS Annual Meeting and Exp., San Diego, CA Apr. 25-28, 2000, Supplement to Inform, 2000, vol. 11, No. 5, p. S91.
Adalbjornsson, et al., "Docosahexaenoic acid in milk of United States women can be increased to recommended values by consumption of two DHA-enriched eggs per day", Nutrition and lactation Post Session I & II, #505 Abstract, ISRHML International Conference, Oct. 4-8, 2002, Mexico City, p. 22.
Borod, et al., "Effects of third trimester consumption of eggs high in docosahexaenoic acid on docosahexaenoic acid status and pregnancy," Lipids, 1999, vol. 34, (supp 1), p. S231 (1999).
Carlson, et al., "A randomized clinical trial of docosahexaenoic acid supplementation during the third trimester of pregnancy and pregnancy outcome," Abstract B-1, presented in May 2002 at the 5th Congress of the International Society for the Study of Fatty Acids and Lipids, p. 44.
Craig-Schmidt, et al., "Phospholipid in DHA-Enriched Eggs as a Source of DHA for Lactating Women", Supplement to Inform, 92nd AOCS Annual Meeting & Expo, Minneapolis, MN May 13-16, 2001, p. S94. Crawford, "Placental delivery of arachidonic and docosahexaenoic acids: implications for the lipid nutrition of preterm infants," Am. J. Clin. Nutr., 2000, vol. 71 (suppl), pp. 275S-284S.
Elmadfa, et al., "Fatty acid profile in baby food products," Eur. J. Lipid Sci. Technol., 2000, pp. 270-275.
Herrera, "Implications of dietary fatty acids during pregnancy on placental, fetal and postnatal development—a review," Placenta, 2002, vol. 23 Supplement A, Trophoblast Research, No. 16, pp. S9-S19.
Mourek, et al., "Essential fatty acids in neonates at risk and in the mother's milk," Cesk Pediatr., Oct. 1993, vol. 48, No. 10, pp. 600-603, Abstract provided, 1 page.
Mydlilova, et al., "The spectrum of fatty acids during lactation in women," Sb Lek, 1993, vol. 94, No. 1, pp. 25-30, Abstract provided, 1 page.
Pszczola, "Innovations Help Baby Foods Grow up", Food Technology, Mar. 2001, vol. 55, No. 3, pp. 52-56.
Tsui, et al., "A survey of dietary supplement use during pregnancy at an academic medical center," Am .J. Obstet. Gynecol., Aug. 2001, vol. 185, No. 2, pp. 433-437.

* cited by examiner

Primary Examiner — San-Ming Hui
Assistant Examiner — Kathrien Cruz
(74) Attorney, Agent, or Firm — Sterne, Kessler, Goldstein & Fox P.L.L.C.

(57) ABSTRACT

A method and product for improving maternal and child health through nutrition. Omega-6 fatty acid and/or omega-3 fatty acid are provided to a woman and/or child prior to, during and/or after pregnancy to improve the health of the woman and her child. The ratios of the omega-6 and omega-3 fatty acids vary during various stages, e.g., pre-pregnancy, pregnancy and post-pregnancy. The omega-6 and omega-3 fatty acids can be in a variety of forms, such as at least one of highly purified algal oil comprising 70% by weight or more of the desired HUFA, triglyceride oil combined with phospholipid, phospholipid, protein and phospholipid combination, or dried marine microalgae.

20 Claims, No Drawings

PRODUCTS CONTAINING HIGHLY UNSATURATED FATTY ACIDS FOR USE BY WOMEN DURING STAGES OF PRECONCEPTION, PREGNANCY AND LACTATION/POST-PARTUM

CROSS-REFERENCE TO RELATED APPLICATIONS

The present application is a continuation of U.S. patent application Ser. No. 10/228,843, filed Aug. 26, 2002, which claims the benefit of priority pursuant to 35 U.S.C. §119(e) to U.S. Provisional Patent Application No. 60/314,713, filed Aug. 24, 2001. The entire disclosures of both applications are incorporated herein by this reference.

FIELD OF THE INVENTION

The present invention is directed to maternal and child nutritional supplements, and in particular maternal and child nutritional supplements that include at least one omega-6 highly unsaturated fatty acid (HUFA) and at least one omega-3 HUFA in certain desired ratios. The ratios of omega-6 HUFA:omega-3 HUFA recommended during various stages vary, for example, the ratios of omega-6 HUFA:omega-3 HUFA can vary between stages of preconception, pregnancy and lactation/postpartum.

BACKGROUND OF THE INVENTION

Currently the scientific literature suggests supplementation with the omega-6 HUFA arachidonic acid (ARA) and the omega-3 HUFA docosahexaenoic acid (DHA) is important for pre-term infant growth and development. Pre-term infants provided with ARA/DHA either from breast milk or enriched infant formula demonstrate improved cognitive abilities, including better vocabulary development, memory, and problem-solving skills, than their unsupplemented counterparts. Pre-term infants fed ARA/DHA have improved visual acuity equivalent to 1 line on an eye exam chart and recent studies suggest these infants also have improved motor skills. The full-term infant literature, however, is not as clear. Several studies have documented similar benefits to full-term infants fed ARA/DHA, however, several have failed to demonstrate any significant benefits. Conflicting studies have led to a hypothesis that differences in maternal HUFA status may be responsible for these conflicting data. DHA is accumulated preferentially to other fatty acids by the fetus during the last intrauterine trimester. When this period is abbreviated, as in premature birth, the accumulation of DHA is limited and hence the response to supplementation may be greater in the pre-term infant. Given a complete third trimester, full-term infants may, depending on the status of maternal supply, acquire adequate, near adequate or insufficient amounts of DHA. The response of full-term infants to HUFA supplementation would be expected to vary significantly and thus the results of studies to date have as well. Due at least in part to these conflicting data, controversy about the use of these fatty acids in infant formulas continues.

U.S. Pat. No. 5,374,657 discloses the combination of DHA and omega-6 gamma linolenic acid (GLA) and the combination of DHA and ARA added to infant formulas. The amount of DHA and ARA present is comparable to the amount present in human breast milk. The GLA is present in an amount that can be converted to an amount of ARA attainable from human breast milk. The GLA, DHA and ARA are preferably triglyceride oils. The amount of the EPA present is much less than the amount of ARA present.

U.S. Pat. No. 6,258,846 discloses a method for enriching the breast milk of a woman to optimize neurological development of an infant breast-fed by the woman by administering one or more of the short chain fatty acids linoleic acid and linolenic acid, together with an omega-3 fatty acid, such as DHA, or an omega-2 fatty acid, prior to and during lactation.

U.S. Pat. No. 5,550,156 discloses triglyceride blends of ARA (omega-6) and DHA (omega-3) or DHA (omega-3) and GLA (omega-6) for use by pregnant or nursing women. The DHA is derived from a microbial oil, preferably triglyceride, with 25 to 40% DHA.

European Patent No. 87101310 discloses blends of ARA (omega-6) and DHA (omega-3) for use in preparing food for infants and premature infants. The recommended DHA to ARA ration is 1:2.0 to 1:3.0 and can be derived from fats of animal or vegetable origin. German Patent No. DE 3920679A1 also discloses a blend of omega-6 HUFA and omega-3 HUFA for use in infant foods in a ratio of 1.0:1 to 5.0:1. Czech Patent No. CZ281096 discloses a fat blend for use in infant milk-based foods derived from fish and vegetable oils that would yield a product containing 26-35% by weight as the described fat blend.

U.S. Pat. No. 5,397,591 discloses the use of DHA (omega-3) from Dinoflagellates (at least 20% DHA) for use in infant food formulation. U.S. Pat. No. 6,149,964 discloses the supplementation of baby food with DHA to be made from egg yolks enriched with DHA omega-3. U.S. Pat. No. 5,869,530 discloses the use of egg derived phospholipids rich in DHA and ARA for use as a dietary supplement for infants, toddlers, and the elderly.

Elmadfa and Majchrzak (2000) recommended, based on a national analysis of infant foods, that both DHA and ARA be added to these foods because these important HUFA were either missing or not provided in adequate amounts in typical infant foods. These authors recommended the combination of vegetable oils and meats to accomplish the availability of HUFA in infant foods. Donald Pszczola, associate editor of Food Technology magazine, highlighted DHA omega-3 as an important nutrient in infant foods and recommended indirect fortification techniques such as adding DHA enriched eggs to accomplish a DHA infant food.

It would be advantageous to supply important HUFA to the developing infant in a more effective, efficient and proactive manner than depending solely on infant formula. It would be advantageous to supply important HUFA to the mother. It would be advantageous to supply important HUFA to the developing infant and mother in a stable form. It would be advantageous to supply important HUFA to the developing infant and mother in a form that is readily bioavailable. It would be advantageous to supply important HUFA to the developing infant and mother in relative amounts that are adjusted to suit the stage of preconception, pregnancy and lactation/postpartum. It would be advantageous to supply the most important essential HUFA to the developing infant (both in utero and postpartum) and mother. It would be advantageous to supply important HUFA to the developing infant and mother in a cost-effective manner. It would be advantageous to supply important HUFA to the developing infant and mother in amounts that alleviate undesired suppression of one or more of the highly unsaturated fatty acids. It would be advantageous to supply important HUFA to the developing infant and mother in specific ratios that help optimize the beneficial effects. It would be advantageous to supply important HUFA to the developing infant and mother in order to promote full-term birth, and preferably, to reduce cognitive and visual delays, increase birth weight and/or improve organ development and function. It would be advantageous to supply important HUFA to the developing infant and mother in order to promote intrauterine growth. It would be advantageous to supply important HUFA to the developing infant and mother in order to decrease the incidence of postpartum depression in the mother. It would be advantageous to provide HUFA to infants/toddlers with sources other than infant formula that have enhanced bioavailability, oxidative stability, and reduced potential for allergenecity.

SUMMARY OF THE INVENTION

In accordance with one embodiment of the present invention, a method is provided for marketing omega-6 highly unsaturated fatty acids (omega-6 HUFA) and omega-3 highly unsaturated fatty acids (omega-3 HUFA) comprising:
 providing at least one product containing at least one omega-6 HUFA and at least one omega-3 HUFA;
 formulating a range of ratios for said omega-6 HUFA and said omega-3 HUFA; and
 marketing said product in a manner to encourage women to take omega-6 HUFA and omega-3 HUFA within said range of ratios during one or more different stages of their preconception, pregnancy and lactation or provide it to a child postpartum.

Preferably, the ratios vary between two or more stages, more preferably, the ratios vary between three or more stages and more preferably, the ratios vary between four or more stages.

In accordance with another embodiment of the present invention, a method for providing HUFA to a mother and child is provided comprising:
 administering omega-6 HUFA to the mother during at least two of the stages of preconception; pregnancy and lactation or to the mother during at least one of the stages of preconception; pregnancy and lactation and to the child during the stage of postpartum;
 administering omega-3 HUFA to the mother during at least two of the stages of preconception; pregnancy and lactation or to the mother during at least one of the stages of preconception; pregnancy and lactation and to the child during the stage of postpartum
 wherein the ratio of said omega-6 HUFA and said omega-3 HUFA vary between at least two of said stages; and,
 wherein the omega-6 HUFA and omega-3 HUFA benefit at least one of the mother and child.

In accordance with another embodiment of the present invention, an omega-6 HUFA and omega-3 HUFA nutritional supplement combination is provided comprising:
 (a) an omega-6 HUFA;
 (b) an omega-3 HUFA;
 wherein said omega-6 and omega-3 HUFA are provided in certain ratios to each other, and
 wherein the ratio of said omega-6 HUFA and said omega-3 HUFA vary between at least two different forms in the combination.

In accordance with another embodiment of the present invention, a perinatal product is provided comprising:
 (a) omega-6 HUFA in the form of at least one of highly purified algal oil comprising 70% or more of the desired HUFA, triglyceride oil combined with phospholipid, phospholipid, protein and phospholipid combination, or dried marine microalgae;
 (b) omega-3 HUFA in the form of at least one of highly purified algal oil comprising 70% or more of the desired HUFA, triglyceride oil combined with phospholipid, phospholipid, protein and phospholipid combination, or dried marine microalgae;
 wherein the omega-6 HUFA and omega-3 HUFA are in a desired range of ratios.

Preferably, the HUFA is in the form of at least one of highly purified algal oil comprising 70% or more of the desired HUFA, triglyceride oil combined with phospholipid, phospholipid, protein and phospholipid combination, or dried marine microalgae. A phospholipid form is desirable, alone or in combination with other materials, due to its stability. Use of triglyceride oils provides flexibility to obtain various desired fatty acid profiles. The oils are easier to blend in oil systems, and the phospholipids are easier to blend in aqueous systems. The algal oil comprising 70% or more of the desired HUFA can be obtained, e.g., by subjecting an algal oil to fractionation, distillation and/or concentration techniques.

Preferably, one or more stages include preconception and stage I pregnancy, stage II pregnancy, stage III pregnancy, and lactation/postpartum. It will be appreciated that during preconception, stage I, stage II and stage III pregnancy and lactation stages the HUFA will be provided to the mother, and during the postpartum stage the HUFA will be provided to the child.

Preferably, the ranges of ratios vary between at least two of said stages.

Preferably, at least one of a woman and a child benefit from the omega-6 HUFA and omega-3 HUFA.

Preferably, at least one of a woman and a child benefit from the omega-6 HUFA and omega-3 HUFA, and wherein said benefit is selected from the group comprising promotion of placental growth, balance of essential fatty acids for placental growth and preliminary growth of the nervous system, improved nervous system growth and development (evidenced by increased cognitive outcomes), improved fetal weight gain, full-term pregnancy and cognitive and visual advantages, increased stature in adulthood, improved opportunities for full organ development and function, decreased incidence of chronic bronchitis in adulthood, decreased risk of gestational diabetes, decreased incidence of postpartum depression, and improved cardiovascular health in adulthood.

Preferably, the range of ratios of omega-6 HUFA:omega-3 HUFA during preconception and stage I pregnancy is from about 1:1 to about 10:1. Preferably, the range of ratios of omega-6 HUFA:omega-3 HUFA during stage II pregnancy is from about 1:10 to about 10:1. Preferably, the range of ratios of omega-6 HUFA:omega-3 HUFA during stage III pregnancy is from about 1:10 to about 5:1. Preferably, the range of ratios of omega-6 HUFA:omega-3 HUFA during lactation/postpartum is from about 1:20 to 1:1.

Preferably, the range of ratios of omega-6 HUFA:omega-3 HUFA during preconception and stage I pregnancy is from about 1:1 to about 10:1; stage II pregnancy is from about 1:10 to about 10:1; stage III pregnancy is from about 1:10 to about 5:1; and lactation/postpartum is from about 1:20 to about 1:1.

Preferably, said omega-3 HUFA comprises at least one of DHA and DPA(n-3). Preferably, said omega-3 HUFA comprises DHA. Preferably, said omega-6 HUFA comprises at least one of DPA(n-6), ARA and dihomo-GLA. Preferably, said omega-6 HUFA comprises at least one of DPA(n-6) and ARA. Preferably, said omega-6 HUFA comprises DPA(n-6).

Preferably, the total fatty acids comprise from about 1% to about 15% DHA; from about 1% to about 6% ARA; from about 0.20% to about 1.0% DPA(n-3); and from about 0.80% to 1.6% DPA(n-6).

Preferably the total fatty acids in a highly purified DHA algal oil comprise from about 70% to about 99% by weight DHA. All percentages are by weight unless stated otherwise or the context indicates otherwise.

Preferably, said product comprises omega-6 HUFA and omega-3 HUFA in a product form selected from the group comprising nutritional supplements, foods, pharmaceutical formulations and beverages. Preferably, said product comprises omega-6 HUFA and omega-3 HUFA in a product form selected from the group comprising infant formula and infant food. Preferably, said product is a food and the levels of HUFA source in said food range from about 0.1% to about 20%.

Preferably, said product comprises one or all of the following in addition to an omega-3 or an omega-6 HUFA: calcium, folic acid, vitamin E, tocotrienols, vitamin D, magnesium, phosphorus, vitamin K, iron, $B_{12}$, niacin, thiamine, riboflavin, biotin, $B_6$, isoflavones and ginger.

DETAILED DESCRIPTION OF THE INVENTION

Dietary fatty acids, in particular ARA and DHA, are involved in promoting full-term birth. The promotion of full-term birth results in healthier infants. The morbidity and mortality associated with pre-term birth is tremendous, with pre-term infants more likely to suffer cognitive and visual delays. Full-term birth (and adequate size at birth) also allows for improved opportunities for full organ development and function. An example is the lungs, fully developed lungs associated with full-term birth and heavier birth weights, have been shown to decrease the incidence of chronic bronchitis in adulthood. Adults with higher birth weights are less likely to suffer or die from cardiovascular disease and suffer from high blood pressure. Therefore, reduced adult cardiovascular-related death and decreased systolic blood pressure are possible outcomes of adequate HUFA supply during preconception and pregnancy. Women consuming DHA from egg phospholipids during the third trimester of pregnancy realized 6±2.3 days longer gestation and delivered infants that were heavier, with a larger head circumference, and greater length at birth. No post-term births were reported in response to this DHA supplementation therefore only the fetal benefits associated with increased time in utero were realized. In addition to benefits to fetal growth and development women supplemented with egg phospholipid DHA experienced significantly reduced labor-related adverse events. One embodiment of the present invention provides for overall improvement of pregnancy outcomes and/or cognitive and visual function and/or full organ development and function related to long-chain HUFA supplementation, and preferably DHA/ARA/DPA supplementation, resulting in promotion of full-term birth.

In accordance with another embodiment of the present invention, an independent effect of long-chain HUFA supplementation on pregnancy outcomes is provided by reducing the incidence of postpartum depression. Supplying long-chain HUFA at varying ratios throughout pregnancy, beginning even before the outset of pregnancy, affords the opportunity to assure the preventative aspects of the present invention. HUFA supplied appropriately throughout the pregnancy process and/or after delivery can pre-empt later issues. For example, postpartum depression is a problem that typically manifests sometime after delivery; the mechanism is unknown and the timing uncertain.

In accordance with another embodiment of the present invention, an effect of long-chain HUFA supplementation on cognitive and visual outcomes is provided by enhancing nervous system development and function independent of birth weight or gestational age. Studies report that nervous system development begins in the third trimester, the "brain growth spurt", and completes near the end of the first year of extra-uterine life. Some studies indicate that cognitive and visual responses are improved in both pre-term and term infants fed HUFA supplemented infant formula. This invention would emphasize the delivery of essential HUFA to support nervous system development when it begins rather than waiting until an infant is born and is related to long-chain HUFA supplementation, and preferably DHA/ARA/DPA supplementation, resulting in promotion of cognitive and visual improvements.

In accordance with another embodiment of the present invention, placental growth is supported. Placental growth is critical to infant growth and even health in adulthood. Research indicates that men born of small placentas are at increased risk of stroke. Therefore, increasing placental size can reduce the risk of stroke in adulthood. ARA has been demonstrated to be a placental growth promoter.

In accordance with another embodiment of the present invention, a method for using a nutritional supplementation scheme that does not result in the suppression of ARA and the subsequent need to replenish it is provided. Infant formula supplementation with DHA requires a balance of ARA to avoid suppression of ARA by DHA below that which is useful to support placental and fetal growth. The combination of DPA(n-6) and DHA(n-3) HUFA maintains higher tissue ARA than DHA alone.

In accordance with another embodiment of the present invention, a method for increasing the stature of infants is provided. Preliminary data from a current Sue Carlson gestation study suggests that maternal DHA supplementation results in longer babies at birth, which may translate to increased stature in adulthood.

In accordance with another embodiment of the present invention, a method for decreasing the incidence of gestational diabetes is provided. Recent research has suggested that women who develop gestational diabetes give birth to infants with DHA levels less than half of that typically reported for full-term infants born of pregnancies not complicated by diabetes. These infants also have been shown to have less mature nervous system consistent with being several weeks premature despite full-term gestational age. Supplementation of DHA during the third trimester of pregnancies complicated by gestational diabetes can help elevate fetal/infant DHA levels closer to those expected for a full-term infant and thus promote a more mature nervous system leading to improved brain and eye development and function.

In accordance with another embodiment of the present invention, maternal nutritional formulations (including nutritional supplements and foods) are provided for each stage of preconception, pregnancy and lactation/postpartum.

In accordance with another embodiment of the present invention, specific ratios of omega-6 and omega-3 highly unsaturated fatty acids are provided for the mother during the stages of preconception, pregnancy and lactation/postpartum in order to provide recommended effective doses of these fatty acids during desired stages. Varying the ratios of omega 6 to omega-3 during various stages of preconception, pregnancy and lactation/postpartum helps provide appropriate levels of HUFA to the mother and/or child to support the physiological processes that are most important during the various stages.

In accordance with another embodiment specific HUFA ratios will be supplied directly to infants through weaning foods such as jarred baby foods or infant cereals. Providing HUFA to infants directly, in addition to the maternal route of supplementation, can assure optimal HUFA supply during critical developmental phases. Providing said HUFA through the form of at least one of highly purified algal oil comprising 70% or more of the desired HUFA, triglyceride oil combined with phospholipid, phospholipid, protein and phospholipid combination, or dried marine microalgae allows more flexibility in the types of foods that can be formulated and the amount of these fatty acids that can be provided than has been previously disclosed. Preferably, the HUFA is provided to the child during the postpartum time period from birth to 24 months of age. Although it is preferred that the HUFA be provided on a daily basis during most of the two years, it can be provided on less than a daily basis for a time period less than two years, as long as desirable results are obtained.

The maternal route of supplementation represents an opportunity to supply these important fatty acids to the developing infant in a more effective and efficient manner than depending solely on infant formula. The prior art method of infant formula supplementation is deficient because the production of the supplement can be expensive, it depletes one important fatty acid (ARA) and therefore requires its simultaneous replacement, it has not considered the entire pregnancy process, it has not considered fetal development, and it has not addressed the instability of long-chain polyunsaturated fatty acid-rich oils.

Infant formula supplementation with DHA requires a balance of ARA to avoid suppression of ARA by DHA below that which is useful to support placental and fetal growth. Using a nutritional supplementation scheme during gestation that does not result in the depression of ARA and the subsequent need for replenishment is a desirable advantage of the present invention. While not wishing to be bound by any theory, it is believed to that DPA(n-6) and DHA supplied simultaneously maintains higher tissue ARA than DHA alone. It is not necessary to add more ARA to counteract the depression by DHA, because DHA supplied in the presence of DPA does not depress ARA, in fact it seems to promote ARA accumulation.

A woman using these products could expect the following improved outcomes for her or her infant:
1) Preconception: maintenance/optimization of membrane integrity to enhance the quality of eggs that may be fertilized;
2) Stage I: promotion of placental growth;
3) Stage II: balance of essential fatty acids (EFA) for placental growth and preliminary growth of the nervous system;
4) Stage III: Nervous system growth and development (evidenced by increased cognitive outcomes); improved fetal weight gain; full-term pregnancy;
5) Lactation/postpartum: Infants receiving HUFA through maternal breast milk may demonstrate cognitive and visual advantages over those provided DHA solely through infant formula during the post-natal period. The mother can also benefit from the HUFA supplementation, as HUFA can provide many health benefits, including reduction in postpartum depression. Therefore, it is unnecessary for the woman to breast-feed in order to achieve benefits from the present invention. Advantages can also be obtained by supplementing the infant's diet using formula and/or food.

In accordance with another embodiment of the present invention, the long-chain fatty acids that are used in the maternal supplements are in a variety of forms. The forms outlined herein allow optimal flexibility in the formulation of foods with high sensory quality, dietary supplements, and pharmaceutical agents. Currently available microalgal oils contain about 40% DHA, extending the DHA content to 70% and above via purification provides a concentrated product that can be useful in products with size constraints, i.e. small serving sizes such as infant foods or dietary supplements with limited feasible pill size. Use of oil and phospholipid combinations helps to enhance the oxidative stability and therefore sensory and nutritional quality of microalgal oil. Oxidative breakdown compromises the nutritional and sensory quality of HUFA in triglyceride form. By employing the phospholipid form, the desired HUFA are more stable and the fatty acids are more bioavailable then when in the triglyceride form. Although microbial oils are vastly more stable the typical fish oils, both are subject to oxidative degradation. Oxidative degradation decreases the nutritional value of these fatty acids. Additionally, oxidized fatty acids are believed to be detrimental to good health. The use of phospholipid DHA/DPA/ARA/dihomo-GLA, a much more stable fatty acid system, assures the health and nutritional value of these supplements. Phospholipids are also easier to blend into aqueous systems than are triglyceride oils. Use of protein and phospholipid combinations allows for the formulation of more nutritionally complex foods as both protein and fatty acids are provided. Use of dried marine microalgae provides high temperature stability for the oil within it and would be advantageous for the formulation of foods baked at high temperature.

Preferably, the source of the desired phospholipids include purified phospholipids from eggs, plant seed oils, and animal organs prepared via the Friolex process and phospholipid extraction process (PEP) (or related processes) for the preparation of nutritional supplements rich in DHA, DPA, ARA and/or dihomo-GLA for use specifically by women preconception, during pregnancy and during lactation/postpartum. The Friolex and PEP, and related, processes are described in greater detail in PCT Patent Nos. PCT/IB01/00841, entitled "Method for the Fractionation of Oil and Polar Lipid-Containing Native Raw Materials" and PCT/IB01/12049, entitled "Method for the Fractionation of Oil and Polar Lipid-Containing Native Raw Materials Using Water-Soluble Organic Solvent and Centrifugation", both filed Apr. 12, 2001, both of which are incorporated herein by reference in their entirety.

Preferably, the highly purified algal oil comprising 70% or more of the desired HUFA, triglyceride oil combined with phospholipid, phospholipid, protein and phospholipid combination, or dried marine microalgae comprise fatty acid residues selected from the group made up of DHA and/or DPA (n-3) and/or DPA(n-6) and/or ARA and/or dihomo-GLA. More preferably, the highly purified algal oil comprising 70% or more of the desired HUFA, triglyceride oil combined with phospholipid, phospholipid, protein and phospholipid combination, or dried marine microalgae comprise fatty acid residues selected from the group made up of DHA, ARA or DPA(n-6). More preferably, the highly purified algal oil comprising 70% or more of the desired HUFA, triglyceride oil combined with phospholipid, phospholipid, protein and phospholipid combination, or dried marine microalgae comprise fatty acid residues selected from the group made up of DHA and DPA(n-6).

Preferably, the maternal supplement comprises from about 20% to about 80% total fatty acid (TFA) as DHA; and/or from about 5% to about 60% TFA as ARA; and/or from about 1% to about 5% TFA as DPA(n-3); and/or from about 1% to about 20% TFA as DPA(n-6). During stage 1 the supplement preferably contains ginger to reduce nausea and vomiting associated with morning sickness.

The ratios of the various fatty acids administered during different stages of preconception, pregnancy and lactation/postpartum are preferably:

Preconception & Stage I pregnancy: ARA+DPA(n-6):DHA—1:1 to 10:1

Stage II pregnancy: ARA+DPA(n-6):DHA—1:10 to 10:1

Stage III pregnancy: ARA+DPA(n-6):DHA—1:10 to 5:1

Lactation: ARA+DPA(n-6):DHA—1:20 to 1:1

The ratios of the various fatty acids administered during different stages of preconception, pregnancy and lactation/postpartum are more preferably:

Preconception & Stage I pregnancy: ARA+DPA(n-6):DHA—about 1:1 to 9:1

Stage II pregnancy: ARA+DPA(n-6):DHA—about 1:5 to 5:1

Stage III pregnancy: ARA+DPA(n-6):DHA—about 1:5 to 2:1

Lactation: ARA+DPA(n-6):DHA—about 1:10 to 1:1

Preconception is defined as the period during which a women is attempting to become pregnant. This is important because preparing for pregnancy is just as important as being pregnant and many women who are trying to become pregnant are pregnant for a month or more before they realize it. Stage I is the first trimester of pregnancy, stage II is the second trimester and stage III is the third trimester. Lactation/postpartum is from delivery until two years later, or until breast-feeding is stopped. It will be understood that supplementation can have benefits for the mother even if the mother is not breast-feeding the child. It will be understood that supplementation is preferred, but not required, during each stage, and is preferred, but not required, continuously throughout each stage.

The ratios of the various fatty acids administered during different stages of preconception, pregnancy and lactation/postpartum are more preferably:

Preconception & Stage I pregnancy: ARA+DPA(n-6):DHA—about 2:1

Stage II pregnancy: ARA+DPA(n-6):DHA—about 1:1

Stage III pregnancy: ARA+DPA(n-6):DHA—about 1:2

Lactation/postpartum: ARA+DPA(n-6):DHA—about 1:3

The daily amounts of the various fatty acids administered during different stages of preconception, pregnancy and lactation/postpartum are preferably:

Preconception & Stage I pregnancy: about 100-300 mg of ARA+DPA (n-6) and about 50-150 mg of DHA and 1 g ginger.

Stage II pregnancy: about 25-200 mg ARA+DPA (n-6) and about 25-200 mg of DHA

Stage III pregnancy: about 25-150 mg ARA+DPA (n-6) and about 50-600 mg of DHA

Lactation/postpartum: about 25-100 mg ARA+DPA(n-6) and about 75-600 mg DHA

Although it is preferred that these amounts be consumed every day, benefits can still be obtained if days are missed.

Preferably, the long-chain HUFA are administered to women in the form of nutritional supplements and/or foods and/or pharmaceutical formulations and/or beverages, more preferably foods, beverages, and/or nutritional supplements, more preferably, foods and beverages, more preferably foods.

Preferably, the long-chain HUFA are administered to infants as infant formula, weaning foods, jarred baby foods, and infant cereals.

Any biologically acceptable dosage forms, and combinations thereof, are contemplated by the inventive subject matter. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables, infusions, health bars, confections, cereals, cereal coatings, foods, nutritive foods, functional foods and combinations thereof. The preparations of the above dosage forms are well known to persons of ordinary skill in the art.

Preferably, foods are enriched with highly purified algal oil comprising 70% or more of the desired HUFA, triglyceride oil combined with phospholipid, phospholipid, protein and phospholipid combination, or dried marine microalgae in a range of about 0.1%-20.0%, more preferably about 0.1-10%, and more preferably about 0.1-3.0%. Preferably, the food that is enriched with the desired HUFA are selected from the group including:

baked goods and mixes; chewing gum; breakfast cereals; cheese products; nuts and nut products; gelatins, pudding, and fillings; frozen dairy products; milk products; dairy product analogs; soft candy; soups and soup mixes; snack foods; processed fruit juice; processed vegetable juice; fats and oils; fish products; plant protein products; poultry products; and meat products;

more preferably, baked goods and mixes; breakfast cereals; gelatins, puddings, and fillings; dairy product analogs; soups and soup mixes; poultry products; nuts and nut products; frozen dairy; milk products; soft candy; plant protein products; fats and oils;

more preferably, nuts and nut products; frozen dairy; milk products; soft candy; plant protein products; fats and oils; and more preferably nuts and nut-based products; milk products; soft candy.

The supplement is preferably administered during one or more of the three stages of pregnancy: preconception, pregnancy, and during lactation/postpartum. Preferably, the supplement is administered during preconception, first or third trimester of pregnancy and during lactation/postpartum. Preferably, the maternal supplement is administered during preconception and during first or third trimester of pregnancy. Preferably, the maternal supplement is administered during preconception and the third trimester of pregnancy.

In accordance with the present invention, supplementation involves long-chain HUFA. Long-chain is defined as twenty carbons or more, thus excluding short-chain fatty acids such as linoleic acid and linolenic acid. Linoleic and linolenic acid have been demonstrated to be ineffective for supplying effective levels of ARA and DHA or resulting in the neurological benefits attributed to ARA/DHA supplementation.

DPA(n-6) is a common fatty acid in the diet, in human tissue, and in human breast milk. However, little research has been conducted regarding its independent health benefits. In fact, because DPA(n-6) is elevated during DHA deficiency, many have focused on DPA(n-6) as negative indicator rather than an important nutrient.

The omega-6 to omega-3 fatty acid ratio has been confirmed by many sources to be very unbalanced. It is generally accepted that we get too much omega-6 fatty acid in our diet, therefore supplementing an omega-6 would seen illogical. However, the principle omega-6 fatty acid in our diet is linoleic acid, a precursor to ARA. Linoleic acid is not utilized to the same degree by the developing placenta/fetus and the conversion of linoleic acid to ARA is limited in both. Therefore, the supplementation of a specific omega-6 fatty acid, ARA or DPA(n-6), is warranted.

Because many studies have indicated that adding ARA/DHA to infant formula improves cognitive skills, the industry has focused on adding these fatty acids to infant formulas. However, the most rapid rate of brain development, "the brain growth spurt", occurs at the beginning of the third trimester and extends to the end of the first year of life. Limiting supplementation to infants limits the impact these fatty acids may have. Maternal supplementation allows for indirect fetal supplementation and the opportunity to optimize neurological outcomes further.

The compositions of the present invention include an omega-3 HUFA and an omega-6 HUFA. Preferred HUFA include omega-3 and omega-6 polyunsaturated fatty acids with three or more double bonds. Omega-3 HUFA are polyethylenic fatty acids in which the ultimate ethylenic bond is three carbons from and including the terminal methyl group of the fatty acid and include, for example, docosahexaenoic acid C22:6(n-3) (DHA) and omega-3 docosapentaenoic acid C22:5(n-3) (DPAn-3). Omega-6 HUFA are polyethylenic fatty acids in which the ultimate ethylenic bond is six carbons from and including the terminal methyl group of the fatty acid and include, for example, arachidonic acid C20:4(n-6) (ARA), C22:4(n-6), omega-6 docosapentaenoic acid C22:5 (n-6) (DPAn-6) and dihomogammalinolenic acid C20:3(n-6) (dihomo GLA). The HUFA are preferably phospholipids.

Any source of HUFA can be used in the compositions and methods of the present invention, including, for example, animal, plant and microbial sources. Sources of the HUFA and methods for processing and isolating the HUFA preferably include those described in U.S. Pat. No. 5,340,594, issued Aug. 23, 1994 and in U.S. Pat. No. 5,698,244, issued Dec. 16, 1997, both incorporated herein by reference in their entirety. For example, strains of fungi, algae or protists can be isolated that contain the HUFA. The organism, such as algae for example, is preferably selected from the orders Dinoflagellates and Thraustochytriales, more preferably from the genus *Crypthecodinium, Thraustochytrium* or *Schizochytrium*, and particularly *Schizochytrium*. Preferred strains are the deposited *Schizochytrium* sp. strains ATCC 20888 and 20889 and derivatives thereof.

Oil seeds, such as soybean, flax, sunflower, safflower, rapeseed and canola for example, are also useful as sources of the HUFA. Preferably, oil seeds that have been genetically modified to increase the HUFA content can be employed. The oil extracted from the seeds can be used. Methods of extracting oil from seeds are known to those skilled in the art. Animal sources, such as fish, can also be used as a source of HUFA.

Preferred sources of the phospholipids include poultry eggs, enriched poultry eggs, algae, fish, fish eggs, genetically engineered (GE) plant seeds or algae; more preferably poultry eggs; enriched poultry eggs; GE plants/algae; non-GE algae; more preferably enriched poultry eggs; GE plants/algae; non-GE algae; more preferably GE plants/algae or non-modified algae.

In addition to the HUFA, additional preferred types of additives include: calcium, folic acid, vitamin-E, tocotrienols, vitamin-D, magnesium, phosphorus, vitamin-K, iron, $B_{12}$, niacin, thiamine, riboflavin, biotin, $B_6$, and ginger. An iron-free version of the nutritional supplement with added ginger would be more preferable.

EXAMPLES

Example 1

Preconception formula containing 200 mg of ARA and 100 mg of DHA, combined with 300 mg of calcium, 100 mcg of folic acid, 200 IU Vitamin D, 150 mg magnesium, 300 mg phosphorus, 25 mcg Vitamin K, 2 mcg B12, and 50% of the DV for each of niacin, thiamine, riboflavin, biotin and $B_6$.

Example 2

First trimester formula containing 200 mg of ARA and 100 mg of DHA, combined with 300 mg of calcium, 100 mcg of folic acid, 200 IU Vitamin D, 150 mg magnesium, 300 mg phosphorus, 25 mcg Vitamin K, 2 mcg B12, and 50% of the DV for each of niacin, thiamine, riboflavin, biotin and $B_6$ and ginger to ease morning sickness.

Example 3

Second trimester formula containing 100 mg ARA and 100 mg of DHA, combined with 300 mg of calcium, 100 mcg of folic acid, 200 IU Vitamin D, 150 mg magnesium, 300 mg phosphorus, 25 mcg Vitamin K, 2 mcg B12, and 50% of the DV for each of niacin, thiamine, riboflavin, biotin and $B_6$.

Example 4

Third trimester formula containing 100 mg ARA and 300 mg of DHA, combined with 300 mg of calcium, 100 mcg of folic acid, 200 IU Vitamin D, 150 mg magnesium, 300 mg phosphorus, 25 mcg Vitamin K, 2 mcg B12, and 50% of the DV for each of niacin, thiamine, riboflavin, biotin and $B_6$.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for improving maternal and child health during the stages of preconception, pregnancy and lactation/postpartum comprising:
   administering a nutritional supplement
   i) to a mother during at least two of the stages of preconception, stage I pregnancy, stage II pregnancy, stage III pregnancy, and lactation, wherein one of the at least two stages is stage III pregnancy, or
   ii) to a mother during at least stage III pregnancy, and to a child during the stage of postpartum;
   wherein the nutritional supplement comprises omega-6 highly unsaturated fatty acid (HUFA) and omega-3 HUFA;
   wherein the nutritional supplement administered during stage III pregnancy comprises arachidonic acid (ARA), docosapentaenoic acid (n-6) (DPA(n-6)), and docosahexaenoic acid (DHA), wherein the ratio of ARA+DPA (n-6):DHA is about 1:2;
   wherein the ratio of omega-6 HUFA and omega-3 HUFA of the nutritional supplement varies between at least two of said stages of i) and ii);
   wherein the ratio of omega-6 HUFA:omega-3 HUFA for administration during preconception and stage I pregnancy is about 1:1 to about 10:1, the ratio of omega-6 HUFA:omega-3 HUFA for administration during stage II pregnancy is about 1:10 to about 10:1, and the ratio of omega-6 HUFA:omega-3 HUFA during lactation/postpartum is about 1:20 to about 1:1; and,
   wherein the nutritional supplement benefits at least one of the mother and the child wherein said benefit is selected from the group consisting of promotion of placental growth, balance of essential fatty acids for placental growth and preliminary growth of the nervous system, improved nervous system growth and development evidenced by increased cognitive outcomes, improved fetal weight gain, full-term pregnancy cognitive and visual advantages, increased stature in adulthood, improved opportunities for full organ development and function, decreased incidence of chronic bronchitis in adulthood, decreased risk of gestational diabetes, decreased incidence of postpartum depression, and improved cardiovascular health in adulthood.

2. The method of claim 1, wherein the omega-6 HUFA is in the form of a triglyceride.

3. The method of claim 1, wherein the omega-3 HUFA is in the form of a triglyceride.

4. The method of claim 1, wherein the omega-6 HUFA is in the form of a phospholipid.

5. The method of claim 1, wherein the omega-3 HUFA is in the form of a phospholipid.

6. The method of claim 1, wherein said omega-3 HUFA administered during preconception, stage I pregnancy, stage II pregnancy, or postpartum comprises at least one of docosahexaenoic acid (DHA) and docosapentaenoic acid (n-3) (DPA(n-3)).

7. The method of claim 1, wherein said omega-6 HUFA administered during preconception, stage I pregnancy, stage II pregnancy, or postpartum comprises at least one of DPA(n-6), arachidonic acid (ARA) and dihomogammalinolenic acid (dihomo-GLA).

8. The method of claim 1, wherein said omega-6 HUFA administered during preconception, stage I pregnancy, stage II pregnancy, or postpartum comprises at least one of DPA(n-6) and ARA.

9. The method of claim 1, wherein said omega-6 HUFA administered during preconception, stage I pregnancy, stage II pregnancy, or postpartum comprises DPA(n-6).

10. The method of claim 1, wherein said omega-6 HUFA and omega-3 HUFA administered during preconception, stage I pregnancy. stage II pregnancy, or postpartum comprise from about 20% to about 80% DHA; from about 5% to about 60% ARA; from about 1% to about 5% DPA(n-3); and from about 1% to about 2% DPA(n-6).

11. The method of claim 1, wherein said nutritional supplement is a product selected from the group consisting of foods, pharmaceutical formulations and beverages.

12. The method of claim 1, wherein said nutritional supplement is a product selected from the group consisting of infant formula and infant food.

13. The method of claim 1, wherein said nutritional supplement is a food.

14. The method of claim 1, wherein said nutritional supplement further comprises one or more of the following: calcium, folic acid, vitamin E, tocotrienols, vitamin D, magnesium, phosphorus, vitamin K, iron, $B_{12}$, niacin, thiamine, riboflavin, biotin, $B_6$, isoflavones and ginger.

15. The method of claim 1, wherein the nutritional supplement is administered to the mother during at least two of the stages of preconception, stage I pregnancy, stage II pregnancy, stage III pregnancy, and lactation wherein one of the at least two stages is stage III pregnancy.

16. The method of claim 1, wherein the nutritional supplement is administered to the mother during at least stage III pregnancy, and to the child during the stage of postpartum.

17. The method of claim 1, wherein the nutritional supplement is administered to the mother during the stage of preconception and stage III pregnancy.

18. The method of claim 1, wherein the nutritional supplement is administered to the mother during the stage of preconception, stage III pregnancy, and the stage of lactation.

19. The method of claim 1, wherein the ratio of omega-6 HUFA:omega-3 HUFA for administration during preconception and stage I pregnancy is about 1:1 to about 9:1, the ratio of omega-6 HUFA:omega-3 HUFA for administration during stage II pregnancy is about 1:5 to about 5:1, and the ratio of omega-6 HUFA:omega-3 HUFA for administration during lactation/postpartum is about 1:10 to about 1:1.

20. The method of claim 1, wherein the ratio of omega-6 HUFA and omega-3 HUFA of the nutritional supplement varies between at least three of said stages of i) and ii).

* * * * *